United States Patent
Ullrich et al.

(10) Patent No.: US 8,815,549 B2
(45) Date of Patent: Aug. 26, 2014

(54) OZONOLYSIS OF UNSATURATED FATTY ACIDS AND DERIVATIVES THEREOF

(71) Applicant: Evonik Degussa GmbH, Essen (DE)

(72) Inventors: Matthias Ullrich, Kassel (DE); Peter Hannen, Herten (DE); Martin Roos, Haltern am See (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/624,141

(22) Filed: Sep. 21, 2012

(65) Prior Publication Data

US 2013/0078685 A1     Mar. 28, 2013

(30) Foreign Application Priority Data

Sep. 23, 2011 (DE) .......................... 10 2011 083 285

(51) Int. Cl.
    *C12P 7/64*          (2006.01)
    *C12N 9/00*          (2006.01)
    *C07C 67/333*      (2006.01)
    *C07C 45/40*        (2006.01)
    *C07C 51/34*        (2006.01)

(52) U.S. Cl.
    CPC .............. *C07C 51/34* (2013.01); *C07C 67/333* (2013.01); *C07C 45/40* (2013.01); *C12P 7/6436* (2013.01)
    USPC .......................................... 435/134; 435/183

(58) Field of Classification Search
None
See application file for complete search history.

(56) References Cited

U.S. PATENT DOCUMENTS 6,828,449 B2    12/2004    Herwig et al.
6,861,540 B2     3/2005    Herwig et al.

OTHER PUBLICATIONS

Heath et al., "A New Sensitive Assay for the Measurement of Hydroperoxides", Analytical Biochemistry, 1976, 76:184-191.*
William A. Pryor, et al., "The Ozonation of Unsaturated Fatty Acids: Aldehydes and Hydrogen Peroxide as Products and Possible Mediators of Ozone Toxicity" Chem. Res. Toxicol., vol. 4, No. 3, 1991, (p. 341-348).
U.S. Appl. No. 13/806,555, filed Dec. 21, 2012, Hannen, et al.
European Search Report issued Feb. 7, 2013 in European Patent Application No. 12181518.7 (with English Translation of Categories of Cited Documents).

* cited by examiner

*Primary Examiner* — Suzanne M Noakes
(74) *Attorney, Agent, or Firm* — Oblon, Spivak, McClelland, Maier & Neustadt, L.L.P.

(57) ABSTRACT

The invention relates to a method for the ozonolysis of unsaturated fatty acids and derivatives thereof, comprising a) ozonolysis of a fatty acid or of a derivative thereof in an organic phase comprising an organic solvent, and b) contacting the organic phase with an aqueous phase comprising catalase and preferably a buffer, where the fatty acid or the derivative thereof has a linear chain having at least eight carbon atoms, and the use of catalase for removing reactive oxygen species from a reaction mixture comprising ozonolysis products of an unsaturated fatty acid.

19 Claims, 1 Drawing Sheet

OZONOLYSIS OF UNSATURATED FATTY ACIDS AND DERIVATIVES THEREOF

CROSS REFERENCE TO RELATED APPLICATIONS

This application claims priority to German Application No. 102011083285.8, filed Sep. 23, 2011, the disclosure of which is incorporated herein by reference in its entirety.

BACKGROUND OF THE INVENTION

The invention relates to a method for the ozonolysis of unsaturated fatty acids and derivatives thereof, and to a method for removing reactive oxygen species from a reaction mixture comprising ozonolysis products of an unsaturated fatty acid or of a derivative thereof.

Ozonolysis is a method established in synthetic organic chemistry for cleaving a C=C double bond of an unsaturated hydrocarbon to form two carbonyl compounds. The latter may in particular be carboxylic acid, aldehydes and alcohols. In mechanistic terms, ozonolysis involves a [3+2]-cycloaddition of the ozone onto the double bond, which gives a primary ozonide, an unstable intermediate, which decomposes to give an aldehyde and a carbonyl oxide. The latter can either polymerize and/or dimerize to give a 1,2,4,5-tetraoxolane or, in a further cycloaddition, form a secondary ozonide. The secondary ozonide can then be worked-up oxidatively to give a carboxylic acid or reductively to give an aldehyde. The aldehyde can be reduced further as far as the alcohol (Vollhardt/Scholer, 1995).

A disadvantage of the method is that from the carbonyl oxide is formed not only the secondary ozonide, which can be worked-up to give the desired products, but also a number of by-products, including the tetraoxolane dimer, an adduct, referred to as hydroperoxide, of ozonide and water and also hydrogen peroxide produced therefrom. Moreover, the formation and accumulation of secondary ozonide is unacceptable with regard to the safety of the reaction implementation since compounds of this type are known to be explosive.

The formation of the other by-products lowers the yield of the reaction, especially since the hydrogen peroxide produced is also able to oxidize products of subsequent steps and, in so doing, to form additional by-products. Undesired carbonyl compounds that are formed can lead to the formation of numerous undesired condensation products.

SUMMARY OF THE INVENTION

Against this background, the problem addressed by the invention consists in providing an improved method in which the appearance of harmful secondary ozonides and troublesome by-products is reduced and the yield of the reaction is accordingly improved.

Thus, an object of the present invention is to develop a method in which the reactive oxygen species in a reaction mixture comprising ozonolysis products of unsaturated fatty acids and derivatives thereof are broken down without consuming reduction equivalents.

A further object of the present invention is to develop a method in which the degradation of the reactive oxygen species in a reaction mixture comprising ozonolysis products of unsaturated fatty acids and derivatives thereof is achieved by an alternative catalyst which has improved properties compared to catalysts used hitherto.

Another object of the present invention is to develop a method in which the treatment of a reaction mixture, comprising ozonolysis products of unsaturated fatty acids and derivatives thereof for the purposes of reducing the concentration of secondary ozonides, takes place under neutral conditions in order to avoid secondary reactions of aldehydic ozonolysis products favoured by extreme pH values.

An additional object of the invention is to improve the method such that it results in an accelerated degradation of reactive oxygen species without requiring a change of solvent.

These and other objects have been achieved by the present invention, the first embodiment of which includes a method for the ozonolysis of unsaturated fatty acids and derivatives thereof, comprising:

a) ozonolysis of the unsaturated fatty acid or derivative thereof in an organic phase comprising an organic solvent; and b) contacting the organic phase with an aqueous phase comprising catalase and optionally, a buffer;

wherein the unsaturated fatty acid or the derivative thereof comprises at least one linear carbon chain of at least eight carbon atoms.

In a preferred embodiment, the unsaturated fatty acid or the derivative thereof is a compound of formula (I):

wherein $R^1$ is selected from the group consisting of hydrogen, HO—, HS—, CHO—, $R^2OC$—, unsubstituted or substituted alkyl, cycloalkyl, heterocycloalkyl, aryl and heteroaryl, $R^2$ is selected from the group consisting of HO—, substituted or unsubstituted alkoxy, alkenoxy, alkynoxy and cycloalkoxy having one to seven carbon atoms, —$NR^3R^4$, aryloxy and benzyloxy, $R^3$ and $R^4$ are each independently selected from the group consisting of hydrogen, alkyl, alkenyl, alkynyl, aryl and benzyl, and x and y, are each, independently, 0 or a larger integer.

In an alternative embodiment, an aqueous phase is contacted with the organic phase during the ozonolysis, and is separated and removed from the organic phase prior to contacting the organic phase with the aqueous phase comprising catalase.

In a further embodiment, the present invention provides a method for removing reactive oxygen species from a reaction mixture comprising ozonolysis products of an unsaturated fatty acid or a derivative thereof, comprising: contacting the reaction mixture with a catalase.

DETAILED DESCRIPTION OF THE INVENTION

In a first embodiment, the present invention provides a method for the ozonolysis of unsaturated fatty acids and derivatives thereof, comprising:

c) ozonolysis of the unsaturated fatty acid or derivative thereof in an organic phase comprising an organic solvent; and d) contacting the organic phase with an aqueous phase comprising catalase and optionally, a buffer;

wherein the unsaturated fatty acid or the derivative thereof comprises at least one linear carbon chain of at least eight carbon atoms.

In a preferred embodiment, the unsaturated fatty acid or the derivative thereof is a compound of formula (I):

$$R^1—(CH_2)_x—CH=CH—(CH_2)_y—COR^2 \qquad (I),$$

wherein $R^1$ is selected from the group consisting of hydrogen, HO—, HS—, CHO—, $R^2OC$—, unsubstituted or substituted alkyl, cycloalkyl, heterocycloalkyl, aryl and heteroaryl, $R^2$ is selected from the group consisting of HO—, substituted or unsubstituted alkoxy, alkenoxy, alkynoxy and cycloalkoxy having one to seven carbon atoms, —$NR^3R^4$, aryloxy and benzyloxy, $R^3$ and $R^4$ are each independently selected from the group consisting of hydrogen, alkyl, alkenyl, alkynyl, aryl and benzyl, and x and y, are each, independently, 0 or a larger integer.

In an alternative embodiment, an aqueous phase is contacted with the organic phase during the ozonolysis, and is separated and removed from the organic phase prior to contacting the organic phase with the aqueous phase comprising catalase.

In a further embodiment, the present invention provides a method for removing reactive oxygen species from a reaction mixture comprising ozonolysis products of an unsaturated fatty acid or a derivative thereof, comprising: contacting the reaction mixture with a catalase.

The organic solvent is an organic solvent which, in the presence of an aqueous phase at room temperature, forms an organic phase separate from the aqueous phase.

The unsaturated fatty acid or the derivative thereof is a compound of the formula (I)

$$R^1—(CH_2)_x—CH=CH—(CH_2)_y—COR^2 \qquad (I),$$

wherein $R^1$ is selected from the group which comprises hydrogen, HO—, HS—, CHO—, $R^2OC$—, unsubstituted or substituted, preferably halogenated, alkyl, cycloalkyl, heterocycloalkyl, aryl and heteroaryl, wherein $R^2$ is selected from the group which comprises HO—, substituted or unsubstituted alkoxy, alkenoxy, alkynoxy and cycloalkoxy having one to seven carbon atoms, —$NR^3R^4$, aryloxy and benzyloxy, where $R^3$ and $R^4$ in each case, and independently of one another, are selected from the group which comprises hydrogen, alkyl, preferably methyl or ethyl, alkenyl, alkynyl, aryl and benzyl, and where x and y, in each case and independently of one another are 0 or a larger integer.

In a preferred embodiment, $R^1$ is hydrogen, $R^2$ is HO—, methoxy or ethoxy and the sum of x and y is nine or more.

The fatty acid or the derivative may be selected from the group which comprises oleic acid and erucic acid and esters thereof, preferably methyl or ethyl esters.

The organic solvent may be selected from the group which comprises compounds of the formula:

$$R^5R^6R^7C—O—R^8$$

or intramolecular ethers thereof, where $R^5$, $R^6$ and $R^7$ in each case, and independently of one another, are selected from the group which comprises hydrogen, an alkyl or cycloalkyl having one to seven carbon atoms, and also unsubstituted and substituted aryl, where $R^8$ is selected from the group which comprises hydrogen, an alkyl, cycloalkyl, hydroxyalkyl and alkoxyalkyl having one to seven carbon atoms, and unsubstituted or substituted aryl and benzyl, and where preferably at least one of the radicals $R^5$, $R^6$ and $R^7$ is methyl.

In a especially preferred embodiment the organic solvent may be a compound of the formula:

$$R^5R^6R^7C—OH,$$

wherein $R^5$, $R^6$ and $R^7$ are, in each case and independently of one another, selected from the group which comprises methyl, ethyl, propyl, butyl and pentyl.

In a highly preferred embodiment, the organic solvent is 2-methyl-2-butanol.

The volume fraction of the aqueous phase upon contacting the organic phase, relative to the total volume of both phases, may be from more than 0 to 50, more preferably 5 to 30, even more preferably 15 to 25 percent.

The catalase may be present in step a).

Preferably, the catalase is beef liver catalase or a variant thereof.

The pH of the aqueous phase in step b), before contacting with the organic phase, is 3 to 11, preferably 5 to 8, yet more preferably 6.5 to 7.5. The pH may be controlled by addition of a buffer system as is conventionally known.

The present invention also provides a method for removing reactive oxygen species, preferably organic reactive oxygen species, from a reaction mixture comprising ozonolysis products of an unsaturated fatty acid or a derivative thereof by contacting catalase with the reaction mixture. The unsaturated fatty acid or the ester thereof may be a compound of formula (I):

$$R^1—(CH_2)_x—CH=CH—(CH_2)_y—COR^2 \qquad (I),$$

wherein $R^1$ is selected from the group which comprises hydrogen, HO—, HS—, CHO—, $R^2OC$—, unsubstituted or substituted, preferably halogenated, alkyl, cycloalkyl, heterocycloalkyl, aryl and heteroaryl, wherein $R^2$ is selected from the group which comprises HO—, substituted or unsubstituted alkoxy, alkenoxy, alkynoxy and cycloalkoxy having one to seven carbon atoms, —$NR^3R^4$, aryloxy and benzyloxy, where $R^3$ and $R^4$ in each case, and independently of one another, are selected from the group which comprises hydrogen, alkyl, preferably methyl or ethyl, alkenyl, alkynyl, aryl and benzyl, and where x and y, in each case and independently of one another are 0 or a larger integer.

The reaction mixture may further comprise an organic solvent, preferably one which, in the presence of an aqueous phase at room temperature, forms an organic phase separate from the aqueous phase, where the organic solvent may be selected from the group of compounds of the formula:

$$R^5R^6R^7C—O—R^8$$

or intramolecular ethers thereof, where $R^5$, $R^6$ and $R^7$ in each case, and independently of one another, are selected from the group which comprises hydrogen, an alkyl or cycloalkyl having one to seven carbon atoms, and also unsubstituted and substituted aryl, where $R^8$ is selected from the group which comprises hydrogen, an alkyl, cycloalkyl, hydroxyalkyl and alkoxyalkyl having one to seven carbon atoms, and unsubstituted or substituted aryl and benzyl, and where preferably at least one of the radicals $R^5$, $R^6$ and $R^7$ is methyl, and where the organic solvent is yet more preferably 2-methyl-2-butanol.

In another aspect, the invention provides a reaction mixture comprising on the one hand an organic phase comprising ozonolysis products of an unsaturated fatty acid or of a derivative thereof, and an organic solvent and on the other hand, an aqueous phase comprising catalase and preferably a buffer, where the fatty acid or the derivative thereof has a linear chain having at least eight carbon atoms. The organic solvent, in the presence of an aqueous phase at room temperature, forms an organic phase separate from the aqueous phase. In a special embodiment of this aspect, the ozonolysis of step a) may take place in the presence of an aqueous phase, which may be separated and removed prior to contacting the ozonolysis reaction mixture with the catalase containing aqueous phase in step b).

In this embodiment, the unsaturated fatty acid or the derivative thereof may be a compound of the formula (I)

$$R^1-(CH_2)_x-CH=CH-(CH_2)_y-COR^2 \qquad (I),$$

wherein $R^1$ is selected from the group which comprises hydrogen, HO—, HS—, CHO—, unsubstituted or substituted, preferably halogenated, alkyl, cycloalkyl, heterocycloalkyl, aryl and heteroaryl, wherein $R^2$ is selected from the group which comprises HO—, substituted or unsubstituted alkoxy, alkenoxy, alkynoxy and cycloalkoxy having one to seven carbon atoms, —$NR^3R^4$, aryloxy and benzyloxy, wherein $R^3$ and $R^4$ in each case, and independently of one another, are selected from the group which comprises hydrogen, alkyl, preferably methyl or ethyl, alkenyl, alkynyl, aryl and benzyl, and wherein x and y, in each case and independently of one another are 0 or a larger integer.

In a highly preferred embodiment of this method, $R^1$ is hydrogen, $R^2$ is hydrogen or methyl or ethyl and the sum of x and y is nine or more.

In a further highly preferred embodiment, the fatty acid or derivative may be selected from the group which comprises oleic acid and erucic acid and esters thereof, preferably methyl or ethyl esters.

In any of these embodiments, the organic solvent may be selected from the group which comprises compounds of the formula:

$$R^5R^6R^7C-O-R^8$$

or intramolecular ethers thereof, where $R^5$, $R^6$ and $R^7$ in each case, and independently of one another, are selected from the group which comprises hydrogen, an alkyl or cycloalkyl having one to seven carbon atoms, and also unsubstituted and substituted aryl, where $R^8$ is selected from the group which comprises hydrogen, an alkyl, cycloalkyl, hydroxyalkyl and alkoxyalkyl having one to seven carbon atoms, and unsubstituted or substituted aryl and benzyl, and where preferably at least one of the radicals $R^5$, $R^6$ and $R^7$ is methyl.

In a special extension of the foregoing embodiment, the organic solvent may be a compound of the formula $$R^5R^6R^7C-OH,$$

and $R^5$, $R^6$ and $R^7$ in each case, and independently of one another, are selected from the group which comprises methyl, ethyl, propyl, butyl and pentyl. The organic solvent according to the foregoing formula may preferably be 2-methyl-2-butanol.

The volume fraction of the aqueous phase upon contacting the organic phase, relative to the total volume of both phases, may be from more than 0 to 50, more preferably 5 to 30, even more preferably 15 to 25 percent.

The catalase may be present during the ozonolysis of step a) and in a highly preferred embodiment the catalase is beef liver catalase or a variant thereof.

The pH of the aqueous phase containing catalase in step b), before contacting with the organic phase, may be from 3 to 11, preferably 5 to 8, more preferably 6.5 to 7.5.

The inventors of the present invention have surprisingly found that the efficiency and yield of the ozonolysis of unsaturated fatty acids and derivatives thereof, and also the purity of the reaction products may be increased by the presence of catalase in the reaction mixture after carrying out the ozonolysis. The inventors have also surprisingly found that the activity of catalase is compatible with the reaction mixture that is formed during the ozonolysis. Finally the inventors have surprisingly found that the presence of catalase in the ozonolysis reaction mixture reduces the concentration of reactive oxygen species such as secondary ozonide as well as the formation of further by-products, and increases the rate of formation of the carbonyl products.

In a preferred embodiment, the term "ozonolysis" as used herein, means a method in which a C=C double bond of a hydrocarbon, more preferably an unsaturated fatty acid or a derivative thereof, is oxidatively cleaved as a result of the action of ozone on the molecule to form carbonyl products. The methods, agents and instruments suitable for carrying out the ozonolysis are conventionally known (Baily, 1978). Conventionally, ozonolysis is carried out in alcohols as solvents, the reaction mixture further comprising at least 0.5 percent by weight of water, based on the total amount of solvent. Usually, the unsaturated fatty acid or its derivative is present in a concentration of 0.1 to 1 mol/l. The ozonolysis is carried out preferably at temperatures from 0 to 40° C., more preferably at temperatures from 10 to 35° C., and particularly preferably at temperatures from 20 to 30° C. Usually, to produce the ozone, an ozone generator is used which uses technical-grade air or a mixture of carbon dioxide and oxygen as feed gas. The ozone is produced from the oxygen by means of non-luminous electric discharge. In the process, oxygen radicals are formed which form ozone molecules with further oxygen molecules.

A particular strength of the method according to the invention may be that an improvement may be achieved by adding an enzymatic activity, not by using aggressive or hazardous compounds and/or reaction conditions. The use of active enzymes in organic synthesis has hitherto primarily been limited to methods on a small scale. Enzymes are not only high-cost agents with low substrate specificity, but are incompatible with numerous solvents customary in organic synthesis on account of various effects, and their use is in many cases still a prerequisite for economical work-up of the desired reaction products. As polypeptides, enzymes generally have a more or less globular structure which is in particular stabilized by the fact that the aliphatic amino acid side chains form a hydrophobic core on the inside, whereas hydrophilic, polar amino acid side chains predominate at the surface of the enzyme. Accordingly, for its stabilization, the enzyme requires a hydrate sheath made of water molecules and has a tendency towards denaturation when it is in contact with a solvent which competes with it for a few available water molecules. In the case of biphasic systems comprising an aqueous phase and an organic phase, interfacial effects often result which can include an absorption and inactivation of the enzyme molecules at the phase boundary. The presence of organic solvents can also influence the kinetic properties of the enzyme, i.e. its activity and its selectivity, for example as a result of reversible or irreversible denaturation of the enzyme or as a result of changing its selectivity or as a result of influencing the reaction equilibrium. Also, the reliable establishment of a certain pH range, which is essential for the activity of enzymes, is difficult in the presence of organic solvents (Wong, 1994).

The term "catalase" as used herein, is understood to mean an enzymatically active polypeptide which catalyzes the decomposition of hydrogen peroxide to give water and oxygen. In a preferred embodiment a catalysis is present if the decomposition of hydrogen peroxide proceeds more rapidly in the presence of detectable amounts of the catalytically effective polypeptide than its absence. In one preferred embodiment, the enzymatically active polypeptide is a multifunctional enzyme which, besides the catalase activity has one or more than one further activity. Examples of polypeptides which may be used according to the invention include beef liver catalase (database code NP_001030463), horseradish peroxidase, for example database code, CAA00083.1, all other catalases described in the prior art (Abad-Zapatero, 1992; Abe et al. 1973, Altomare et al., 1974, Baird et al, 1987), Balasubramaniam et al., 1987; Barlow & Margoliash, 1969; Beers & Sizer, 1952; Beyer & Fridovich, 1985; Boismenu et al., 1989; Browett & Stillman, 1980; Chance, 1951; Chance, 1955, Chance, 1973, Chance et al., 1973; Chatterjee et al., 1989; Ch et al., 1975; Corrall et al., 1974; Darr & Fridovich, 1985; Davison et al., 1986; Deisseroth & Dounce, 1969; Diesseroth et al., 1967; Eglinton et al., 1983; Escobar et al., 1990; Evans & Recheigl, 1967; Feinstein et al., 1967; Feinstein et al, 1967; Fita & Rossman, 1985; Furuta et al., 1974; Ghadermarzi & Moosavi-Movahedi, 1996; Goldacre & Galston, 1953; Goldstein, 1968; Goth, 1989; Goth, 1991; Gregory & Fridovich, 1974; Gadermarzi & Moosavi-Movahedi, 1996; Goldacre & Galston, 1953; Goldstein, 1968; Goth, 1989; Goth, 1991; Gregory & Fridovich, 1974; Haining & Legan, 1972; Halliwell, 1973; Heidrich, 1968, Higashi et al., 1974; Holmes, 1972; Holmes & Masters, 1972; Johansson & Borg, 1988; Jones & Masters, 1975; Jones, 1973; Jones & Middlemiss, 1972; Kirkman & Gaetani, 1984; Kiselev et al., 1967; Kremer, 1970; Kroll et al., 1989; Kyle et al., 1987; Lanir & Schejter, 1975; Lardinois, 1995; Lee et al., 1987; Liebermann & Ove, 1958; Loewen & Seitala, 1987; Longley, 1967; Maehly & Chance, 1954; Maimoni et al., 1999; Margoliash & Novogorodsky, 1958; Marklund, 1972, Mastersc, 1986; McPherson & Rich, 1973; Mitchel & Anderson, 1965; Miyahara et al., 1978; Murphy et al., 1967; Madler et al., 1986; Nelson & Niesow, 1972M Nicholls et al., 1963; Orr, 1967a; On, 1967b; Oshino et al., 1973; Percy et al., 1990; Perrin et al., 1990; Pitts, 1992; Poznansky et al., 1974; Pritchard & Hudson, 1967; Roth & Jensen, 1967; Rossman & Labaw, 1967; Sakamoto & Highashi, 1974; Samejima; Kita, 1969; Samejima et al., 1962; Schroeder et al., 1969; Scibior & Czeczot, 2006; Scott et al., 1991; Seah & Kaplan, 1973; Seah et al., 1973; Sharma et al., 1989; Shimiza et al., 1984; Spreti et al., 1995; Sumner & Dounce, 1937; Sumner et al., 1940; Sund et al., 1967; Tanaka et al., 1991; Tanford & Lovrien, 1962; Tauber & Petit, 1952; Tudhope, 1967; Vuilaum et al., 1988; Wheeler et al., 1990; Whiteside et al., 1988; Yasukochi et al., 1972; Zidoni & Kremer, 1974) and variants thereof.

If, for the activity of the catalase, as well as hydrogen peroxide, a further substrate and/or one or more than one co-factor is also required, the catalase comprises this. E.g. in the case of using horseradish peroxidase, the presence of 2,2'-azinobis(3-ethylbenzothiazoline-6-sulphonic acid) is required.

The catalase used may be added to the reaction mixture in different forms and in different purification stages, from an unprocessed solution or a pellet of cells having catalase activity ranging to a completely purified enzyme. In a preferred embodiment, the catalase may be a polypeptide associated with a whole, either viable or lysed cell, for example one which is expressed by a prokaryotic whole-cell catalyst, preferably bacterial in nature. In this connection, a cell, if it is used as a whole-cell catalyst does not have to express the catalase on its inside, but a catalase localized on the outer membrane is also possible, for example a fusion protein with an endogenous outer membrane protein. In a further preferred embodiment, the lysate is a cell, preferably bacterial in nature, which expresses the catalase in the inside of the cell. In a further embodiment, it is a solution or a lyophilizate or a lyophilizate, preferably at least 60, 70, 80, 90 or 95, particularly preferably 100% pure, polypeptide. Preparations of these types of cells or polypeptides are commercially available or can be produced for the person skilled in the art by reference to standard biochemical methods.

The concentration of the catalase in one preferred embodiment may be 0.001 to 1, more preferably 0.1 to 0.5, most preferably 0.025 to 0.1 percent by weight of the aqueous phase in step b).

The sequence and implementation of steps a) and b) may take place in all conceivable variations provided the catalase comes into contact with the products of the ozonolysis of the fatty acid or of the derivative thereof. Whereas the presence of an aqueous phase comprising catalase is essential in step b), it is optional in step a). Thus, the same aqueous phase can be present in step a) and b), although it is also possible to carry out step a) in the presence of one aqueous phase, but to remove this and to use a different aqueous phase for step b). Likewise it is possible to add an aqueous phase with or without catalase to the organic phase during or before step a) and to add the catalase to the aqueous phase when the ozonolysis in step a) is complete. In one particularly preferred embodiment, the catalase is only added to the organic phase after the ozonolysis.

Numerous methods and protocols according to which catalytically active catalases can be purified from wild-type cells or recombinant cells are known to the person skilled in the art, see for example Yumoto et al., 2000.

Suitable starting materials for the ozonolysis are all conceivable fatty acids and derivatives thereof, both naturally occurring ones and also artificially synthesized ones, those with an even or uneven number of carbon atoms and branched and also unbranched ones, in particular undecylenic acid, myristoleic acid, palmitoleic acid, petroselic acid, oleic acid, elaidic acid, vaccenic acid, gadoleic acid, icosenic acid, cetoleic acid, erucic acid, nervonic acid and derivatives thereof, preferably their methyl esters. Furthermore, it is also possible to use polyunsaturated fatty acids, for example linoleic acid, linolenic acid, calendic acid, punicic acid, elaeostearic acid, arachidonic acid, timnodonic acid, clupanodonic acid and cervonic acid and derivatives thereof, preferably their methyl esters. In one preferred embodiment, the fact that "the fatty acid or the derivative thereof has a linear chain with at least eight carbon atoms", as used herein, means that the carbon atom of the carboxyl group is part, preferably at the end, of a linear chain having at least eight carbon atoms which must have branches if the length of eight carbon atoms is given over the longest possible linear chain in the carbon backbone.

In one preferred embodiment, the substituents referred to as "alkoxy", "alkenoxy" or "alkynoxy" as used herein, are substituents of the formula R—O—, where R is an alkyl, alkenyl or alkynyl.

A particular advantage of the method according to the invention may be that ozonolysis and removal of the reactive oxygen species may be carried out in solvents or solvent mixtures compatible with both reactions, i.e. in a one-pot reaction, meaning that a complex change of solvent may be omitted. In a preferred embodiment, step b) may be accordingly carried out in the same reaction vessel without changing the solvent or without separating off constituents of the reaction mixture from step a).

In one particular embodiment, the volume fraction of the aqueous phase upon contacting the organic phase, based on the total volume of both phases, is more than 0.5, 1, 5, 10, 15, 20, 25 or more than 0 to 50, more than 1 to 40, more than 2.5 to 25, more preferably 5 to 30, even more preferably 15 to 25 percent. These ranges and sub-ranges include all values therebetween as do all ranges and sub-ranges described throughout this specification.

In principle, a large number of solvents may be used for step a), for example aliphatics such as hexane or cyclohexane, aromatics alkylated aromatics such as benzene, toluene or xylene, halogenated aliphatics or aromatics such as dichloromethane or chlorobenzene, ketones, for example acetone or cyclohexanone, alcohols and ethers thereof such as 2-butanol, 2-methyl-2-propanol or methyl tert-butyl ether, carboxylic acids and esters thereof, such as acetic acid or ethyl acetate, sulphoxides such as dimethyl sulphoxide, and heterocycles such as tetrahydrofuran or dioxane. Particularly preferred solvents include secondary and tertiary alcohols, including in particular 2-propanol and tert-butanol. If the solvent is a solvent of the formula $R^5R^6R^7C\text{—}O\text{—}R^8$, then the radicals $R^5, R^6, R^7$ and $R^8$ may, in each case in pairs and independently of one another, form alkylene bridges of the formula $\text{—}(CH_2)_z\text{—}$, where z is selected such that the corresponding ring has at least 3, preferably at least 5, members. Furthermore, the radicals can also form intramolecular ethers, which are formally the result of the condensation of two hydroxy-containing radicals. For example, for the case that $R^5\text{=}R^6\text{=}$methyl, $R^7$ is hydroxypropyl and $R^8$ is hydrogen, a solvent according to the invention is the compound with the formula Methods for separating off the organic solvents, particularly if these form a phase separate from the aqueous phase without assistance, are known by a person skilled in the art and may take place for example by means of decanting, use of a separating funnel and the like.

In one preferred embodiment, the term "an organic phase separate from the aqueous phase", as used herein, is understood as meaning a homogeneous liquid phase consisting, at room temperature, predominantly preferably to at least 90 volume percent, of organic solvents which, after contacting with an aqueous phase, settles from this without further assistance, as may preferably be established by purely visible means, and resulting, after the equilibrium has been established, in the formation of two separate phases.

Steps a) and b) may be followed by a further processing of the ozonolysis product freed from reactive oxygen species. For example, the reductive amination is possible, in which an aldehyde or ketone is aminated, i.e. in the case of an ci-oxocarboxylic acid ozonolysis product the result is the formation of an ω-aminocarboxylic acid. Such a reductive amination is preferably carried out with the aid of a Raney nickel catalyst and hydrogen, as conventionally known, for example, see Chan et al., 1994. Alternatively, a further oxidation to the α,ω-dicarboxylic acid may be useful.

Having generally described this invention, a further understanding can be obtained by reference to certain specific examples which are provided herein for purposes of illustration only, and are not intended to be limiting unless otherwise specified.

The present invention is illustrated further by the following figures and non-limiting examples, which reveal further features, embodiments, aspects and advantages of the present invention.

Figure 1:
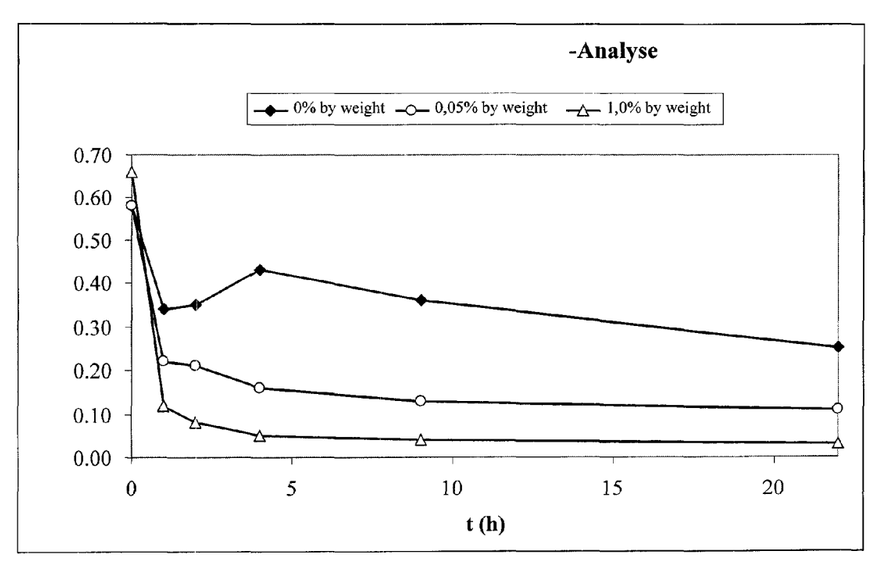
FIG. 1 shows a graph of reactive oxygen species concentration against time when treated according to the present invention.

FIG. 1 shows the reduction in the concentration of reactive oxygen species following the treatment according to the invention of a solution of ozonolysis products with various amounts of lyophilized beef liver catalase, as described in example 1. The y-axis shows the amount of reactive oxygen species in weight percent.

Example 1

Ozonolysis of methyl cis-13-docosenoate (methyl erucate) with Subsequent Catalase Treatment All chemicals and solvents were acquired in the highest possible grade (at least p.a.) on the free market and used without further purification and/or treatment. Water only in demineralized grade. Phosphate buffer solution (pH=7.0) was acquired from Bernd Kraft GmbH (Duisburg, Germany), freeze-dried beef liver catalase from Sigma-Aldrich (St. Louis, USA). The fatty acid esters methyl cis-9-octadecenoate (methyl oleate) and methyl cis-13-docosenoate (methyl erucate) were acquired as 95 percent materials from Croda (Gouda, The Netherlands). According to GC analysis (uncorrected) the purity of the C18:1 or C22:1 methyl ester was 95.2 or 95.0%, respectively. In the case of the methyl oleate, the impurities present were 3.6% of C18:2 methyl esters and also, in total, 1.2% of the saturated methyl esters methyl hexadecanoate, octadecanoate and eicosanoate (methyl palmitate, stearate and arachidate), i.e. 98.8% unsaturated, i.e. cleavable methyl esters. In the case of the methyl erucate, the impurities comprised 1.3% of C22:2 methyl esters, 0.7% of C20:1 methyl esters and 1.0% of C24:1 methyl esters, and, in total, 2.0% of the saturated methyl esters methyl eicosanoate, docosanoate and tetracosanoate (methyl arachidate, behenate and lignocerate), i.e. 98.0% of the starting material were unsaturated, cleavable methyl esters.

A 0.912 mol al two-phase mixture of a solution of 80.0 g of methyl cis-13-docosenoate (methyl erucate) in 160 ml of 2-methyl-2-butanol and 30 ml of water was provided in a conical 250 ml three-neck receiver with bottom discharge (Teflon stopcock). Via the latter, a hose pump was attached, via the middle (NS29-) standard ground glass joint, a trickle bed glass column (800×30 mm) filled with Raschig rings (6×6×0.65 mm) with top and bottom gas feed and top gas discharge. Via one side (NS14-) standard ground glass joint an internal thermometer was attached, the other standard ground glass joint was free (sampling point). Using the pump, the two-phase mixture was circulated at room temperature via the column (flow rate: 120 ml/min). Counter to the flow of solution, a reactive gas of an $O_2/O_3$ mixture was introduced from below the column from an ozone generator (1500 ml/min (stp) $O_2$ stream, maximum generator throughput). From above the column, $CO_2$ was mixed as carrier gas or flushing gas into the $O_3$-depleted $O_2$ discharge (likewise 1500 ml/min (stp)). The off-gas stream flowed via an interconnected cold trap with ice cooling through 100 ml of a 5 percent by weight aqueous potassium iodide solution as ozone indicator. For sampling, a few drops of the reaction mixture were removed by pipette, taken up in 2 ml of ethyl acetate/water (1:1), briefly extracted by shaking, and the organic phase was then analyzed by GC (15 m DB-1 column).

After 65 min, complete mixing of the two phases occurred, after 110 min the reaction was complete (>99.5% conversion or <0.5% remaining starting material), after which the pump was switched off and the introduction of the two gases was ended. The temperature of the reaction mixture increased over the entire time by significantly less than 10° C.

According to GC analysis, the products present in the resulting reaction solution were nonanal and methyl 13-oxo-decanoate in equal parts in a relative purity of >95%; the products of the further oxidation of these two compounds, nonanoic acid (pelargonic acid) and β-hydroxy-13-oxomethyltridecanoate (methyl brassylate), were each found in <5% in the solution.

The product solution was discharged from the apparatus, the emptied apparatus was rinsed with in each case 160 ml of 2-methyl-2-butanol and tetrahydrofuran and the resulting solution was divided into three equal parts each of 200 ml. To each of the three solutions was added 100 ml of a freshly prepared aqueous solution of beef liver catalase in phosphate buffer solution (pH=7.0), the end concentration of the beef liver catalase in the aqueous solution in the first case being 0% by weight (blank sample), in the second case being 0.05% by weight, and in the third case being 1.0% by weight. All three solutions were rinsed again with 100 ml buffer solution. The two-phase mixtures obtained in this way were stirred vigorously at room temperature, and after 1, 2, 4, 9 and 22 h, 40 ml samples were taken in each case and analyzed as to the content of reactive oxygen.

For this, the sample was boiled at reflux under protective gas ($N_2$) in the presence of excess sodium iodide. After cooling, the resulting iodide was titrated potentiometrically with a thiosulphate solution: to the sample of the sample weighed into the Erlenmeyer flask was firstly added dry ice, then 80 ml of 1-propanol, 4 ml of acetic acid, and 20 ml of isopropanolic sodium iodide solution. After a reflux condenser was attached, nitrogen was introduced via the condenser. The reaction mixture was then left to stand for half an hour at room temperature and then boiled for 10 minutes. After cooling, ca. 20 ml of water were flushed through the condenser then the mixture was titrated with 0.01 mol/l of sodium thiosulphate solution to the equivalence point. In parallel, a blank-value determination was carried out in the same way.

The corresponding results are listed in Tab. 1 and FIG. 1.

TABLE 1

Concentration of reactive oxygen species following the addition of different amounts of catalase to a reaction mixture with ozonolysis products and methyl erucate

| Run time (hr.) | 0% by weight lyophilized catalase | 0.05% by weight lyophilized catalase | 1.00% by weight lyophilized catalase |
|---|---|---|---|
| 0 | 0.58 | 0.58 | 0.66 |
| 1 | 0.34 | 0.22 | 0.12 |
| 2 | 0.35 | 0.21 | 0.08 |
| 4 | 0.43 | 0.16 | 0.05 |
| 9 | 0.36 | 0.13 | 0.04 |
| 22 | 0.25 | 0.11 | 0.03 |

It is therefore clearly evident that, compared with the blank sample, the use of a solution of just 0.05% by weight of beef liver catalase reduces the fraction of potentially oxidizing constituents in the organic product solution by a factor >2; when using a solution of 1% by weight beef liver catalase, even a factor of almost 10 results.

Particularly the rapid decrease at the start of the treatment clearly showed that, with the help of such a treatment, it is possible to stabilize product solutions against further oxidation of very labile compounds such as aliphatic aldehydes in this sense.

Numerous modifications and variations on the present invention are possible in light of the above teachings. It is therefore to be understood that within the scope of the appended claims, the invention may be practiced otherwise than as specifically described herein.

LITERATURE SOURCES

Baily, P. S., Ozonation in organic chemistry, Academic: New York, N.Y., 1978, Vol. 1.

Wong, C.-H., Enzymes in synthetic organic chemistry, Elsevier Science Limited, 1994

DE 102011015150.8 (2011): SYNTHESE VON OMEGA-AMINOCARBONSÄUREN UND DEREN ESTERN AUS UNGESÄTTIGTEN FETTSÄUREDERIVATEN [SYNTHESIS OF OMEGA-AMINOCARBOXYLIC ACIDS AND ESTERS THEREOF FROM UNSATURATED FATTY ACID DERIVATIVES]

Vollhardt/Scholer (1995): Organische Chemie [Organic Chemistry], 2nd edition, VCH Yumoto, et al. (2000) Purification and Characterisation of a Catalase from the Facultatively Psychrophilic Bacterium, Vibrio rumoiensis S-1 Exhibiting High Catalase Activity, J. Bact. 182(7), 1903-1909

Abad-Zapatero, C.: Crystallization by Centrifugation, Nature 356, 392, 1992

Abe, K., Hiraga, M., and Anan, F.: The Chemical Modification of Beef Liver Catalase. IV. The Properties of Acrylonitrile- or Glyoxal-Treated Products of Catalase, J Biochem (Tokyo) 74, 889, 1973

Altomare, R., Kohler, J., Greenfield, P., and Kittrell, J.: Deactivation of Immobilized Beef Liver Catalase by Hydrogen Peroxide, Biotechnol Bioeng 16, 1659, 1974

Baird, M., Sfeir, G., and Slade-Pacini, C.: Lack of Inhibition of Mouse Catalase Activity by Cimetidine: An Argument Against a Relevant General Effect of Cimetidine Upon Heme Metabolic Pathways, Biochem Pharmacol 36, 4366, 1987

Balasubramanian, P., Schmidt, E., and Bruice, T.: Catalase Modeling. 2. Dynamics of Reaction of a Water-Soluble and Non u-Oxo Dimer Forming Manganese (III) Porphyrin with Hydrogen Peroxide, J Am Chem Soc 109, 7865, 1987

Barlow, G., and Margoliash, E.: Sedimentation Studies on Catalase Complex II Using Photoelectric Scanning Optics, Biochim Biophys Acta Gene Struct. Expr. 188, 159, 1969

Beers, R., and Sizer, I.: A Spectrophotometric Method for Measuring the Breakdown of Hydrogen Peroxide by Catalase, J Biol Chem 195, 133, 1952

Beyer, W., and Fridovich, I.: Pseudocatalase from Lactobacillus plantarum: Evidence for a Homopentameric Structure Containing Two Atoms of Manganese per Subunit, Biochem 24, 6460, 1985

Boismenu, D., Lepine, F., Gagnon, M., and Dugas, H.: Catalase Activity Measurement with the Disk Flotation Method, Anal Biochem 178, 404, 1989

Browett, W., and Stillman, M.: Magnetic Circular Dichroism Studies on the Electronic Configurations of Catalase Compounds I and II, Biochim Biophys Acta 623, 21, 1980

Chan, A. S. C., Chen, C.-C., and Lin, Y.-C. (1994) Catalytic reductive Amination of □-ketocarboxylic acids as a useful route to amino acids, Applied Catalysis A General 119, L1-L5

Chance, B.: The Iron-Containing Enzymes. C. The Enzyme-Substrate Compounds and Mechanism of Action of the Hydroperoxidases, The Enzymes Vol. 2, Pt. 1, J. Sumner and K. Myrback, Academic Press, NY, 1951

Chance, B., and Maehley, A.: Assay of Catalases and Peroxidases, Meth Enzymol 2, 764, 1955

Chance, B., and Oshino, N.: Analysis of the Catalase-Hydrogen Peroxide Intermediate in Complex Oxidations, Biochem J 131, 564, 1973

Chance, B., Boveris, A., Oshino, N., and Loschen, G.: The Nature of the Catalase Intermediate in the Biological Function, Oxidases and Related Redox Systems Vol. I, T. King, H. Mason, and M. Morrison, University Park Press, Baltimore, USA, 350, 1973

Chatterjee, U., Kumar, A., and Sanwal, G.: Purification and Properties of Goat Liver Catalase—Two pH Optima, Indian J Biochem Biophys 26, 140, 1989

Chu, H., Leeder, J., and Gilbert, S.: Immobilized Catalase Reactor for Use in Peroxide Sterilization of Dairy Products, J Food Sci 40, 641, 1975

Corrall, R., Rodman, H., Margolis, J., and Landau, B.: Stereospecificity of the Oxidation of Ethanol by Catalase, J Biol Chem 249, 3181, 1974

Darr, D., and Fridovich, I.: Inhibition of Catalase by 3,3'-diamine-benzidine, Biochem J 226, 781, 1985

Davison, A., Kettle, A., and Fatur, D.: Mechanism of the Inhibition of Catalase by Ascorbate, J Biol Chem 261, 1193, 1986

Deisseroth, A., and Dounce, A.: Comparison of the Catalytic and Physical Properties of the Components of Lyophilized Beef Erythrocyte Catalase with those of Lyophilized Beef Liver Catalase Components, Arch Biochem Biophys 131, 30, 1969

Diesseroth, A., and Dounce, A.: Nature of the Change Produced in Catalase by Lyophilization, Arch Biochem Biophys 120, 671, 1967

Eglinton, D., Gadsby, P., Sievers, G., Peterson, J., and Thompson, A.: A Comparative Study of the Low-Temperature Magnetic Circular Dichroism Spectra of Horse Heart Metmyoglobin and Bovine Liver Catalase Derivatives, Biochim Biophys Acta 742, 648, 1983

Escobar, L., Salvador, C., Contreras, M., and Escamilla, J.: On the Application of the Clark Electrode to the Study of Enzyme Kinetics in Apolar Solvents: The Catalase Reaction, Anal Biochem 184, 139, 1990

Evans, W., and Recheigl, M.: Factors Influencing Myeloperoxidase and Catalase Activities in Polymorphonuclear Leukocytes, Biochim Biophys Acta 148, 243, 1967

Feinstein, R., Braun, J., and Howard, J.: Acatalasemic and Hypocatalasemic Mouse Mutants. II. Mutational Variations in Blood and Solid Tissue Catalases, Arch Biochem Biophys 120, 165, 1967

Feinstein, R., Sacher, G., Howard, J., and Braun, J.: Comparative Heat Stability of Blood Catalase, Arch Biochem Biophys 122, 338, 1967

Fita, I., and Rossmann, M.: The NADPH Binding Site on Beef Liver Catalase, Proc Natl Acad Sci USA 82, 1985

Furuta, H., Hachimori, A., Ohta, Y., and Samejima, T.: Dissociation of Bovine Liver Catalase into Subunits on Acetylation, J Biochem (Tokyo) 76, 481, 1974

Ghadermarzi, M., and Moosavi-Movahedi, A.: Determination of the Kinetic Parameters for the 'Suicide Substrate' Inactivation of Bovine Liver Catalase by Hydrogen Peroxide, J Enzym Inhib 10, 167-175, 1996

Goldacre, P., and Galston, A.: The Specific Inhibition of Catalase by Substituted Phenols, Arch Biochem Biophys 43, 169, 1953

Goldstein, D.: A Method for Assay of Catalase with the Oxygen Cathode, Anal Biochem 24, 431, 1968

Goth, L.: Human Erythrocyte Catalase, Isolation with an Improved Method, Characterization and Comparison to Bovine Liver Catalase, Enzyme 41, 191, 1989

Goth, L.: A Simple Method for Determination of Serum Catalase Activity and Revision of Reference Range, Clin Chim. Acta 196, 143, 1991

Gregory, E., and Fridovich, I.: Visualization of Catalase on Acrylamide Gels, Anal Biochem 58, 57, 1974

Haining, J., and Legan, J.: Improved Assay for Catalase Based Upon Steady-State Substrate Concentration, Anal Biochem 45, 469, 1972

Halliwell, B.: Superoxide Dismutase: A Contaminant of Bovine Catalase, Biochem J 135, 379, 1973

Heidrich, H.: New Aspects on the Heterogeneity of Beef Liver Catalase, Hoppe Seylers Z Physiol Chem 349, 873, 1968

Higashi, T., Kawamata, F., and Sakamoto, T.: Studies on Rat Liver Catalase. VII. Double-Labeling of Catalase by $^{14}$C-Leucine and $^{3}$H-d-Aminolevulinic Acid, J Biochem (Tokyo) 76, 703, 1974

Holmes, R.: Catalase Multiplicity in Normal and Acatalasemic Mice, FEBS Lett 24, 161, 1972

Holmes, R., and Masters, C.: Species Specific Features of the Distribution and Multiplicity of Mammalian Liver Catalase, Arch Biochem Biophys 148, 217, 1972

Johansson, L., and Borg, L.: A Spectophotometric Method for Determination of Catalase Activity in Small Tissue Samples, Anal Biochem 174, 331, 1988

Jones, G., and Masters, C.: On the Nature and Characteristics of the Multiple Forms of Catalase in Mouse Liver, Arch Biochem Biophys 169, 7, 1975

Jones, P.: The Evolution of Catalase Activity, Oxidases and Related Redox Systems, T. King, H. Mason, and M. Morrison, University Park Press, Baltimore, USA, 333, 1973

Jones, P., and Middlemiss, D.: Formation of Compound I by the Reaction of Catalase with Peroxoacetic Acid, Biochem J 130, 411, 1972

Kirkman, H., and Gaetani, G.: Catalase: A Tetrameric Enzyme with Four Tightly Bound Molecules of NADPH, Proc Natl Acad Sci USA 81, 4243, 1984

Kiselev, N., Shpitzberg, C., and Vainshtein, B.: Crystallization of Catalase in the Form of Tubes with Monomolecular Walls, J Mol Biol 25, 433, 1967

Kremer, M.: Peroxidatic Activity of Catalase, Biochim Biophys Acta 198, 199, 1970

Kroll, R., Frears, E., and Bayliss, A.: An Oxygen Electrode-Based Assay of Catalase Activity as a Rapid Method for Estimating the Bacterial Content of Foods, J Appl Bacteriol 66, 209, 1989

Kyle, M., Miccadei, S., Nakae, D., and Farber, J.: Superoxide Dismutase and Catalase Protect Cultured Hepatocytes from the Cytotoxicity of Acetaminophen, Biochem Biophys Res Commun 149, 889, 1987

Lanir, A., and Schejter, A.: On the Sixth Coordination Position of Beef Liver Catalase, FEBS Lett, 55, 254, 1975

Lardinois, O.: Reactions of Bovine Liver Catalase with Superoxide Radicals and Hydrogen Peroxide, Free Radic Res 22, 251, 1995

Lee, K., Cronenwett, J., Shlafer, M., Corpron, C., and Zelenock, G.: Effect of Superoxide Dismutase Plus Catalase on $Ca^{2+}$ Transport in Ischemic and Reperfused Skeletal Muscle, J Surg Res 42, 24, 1987

Lieberman, I., and Ove, P.: Catalase Requirement for Mammalian Cells in Culture, J Exp Med 108, 631, 1958

Loewen, P., and Seitala, J.: Purification and Characterization of Catalase-1 From *Bacillus subtilis, Biochem Cell Biol* 65, 939, 1987

Longley, W.: The Crystal Structure of Bovine Liver Catalase: A Combined Study by N-ray Diffraction and Electron Microscopy, J Mol Biol 30, 323, 1967

Maehly, A., and Chance, B.: The Assay of Catalases and Peroxidases, in, Methods of Biochemical Analysis, 357, 1954

Maimoni Goncalves, V., Cezar de Cerqueira Leite, L., Raw, I., and Cabrera-Crespo, J.: Purification of Catalase from Human Placenta, Biotechnol Appl Biochem 29, 73, 1999

Margoliash, E., and Novogrodsky, A.: A Study of the Inhibiton of Catalase by 3-Amino-1:2:4 Triazole, Biochem J 68, 468, 1958

Marklund, S.: Interactions Between Hydroxymethylhydroperoxide and Catalase, Biochim Biophys Acta 289, 269, 1972

Masters, C., Pegg, M., and Crane, D.: On the Multiplicity of the Enzyme Catalase in Mammalian Liver, Mol Cell Biochem 70, 113, 1986

McPherson, A., and Rich, A.: Crystallographic Study of Beef Liver Catalase, Arch Biochem Biophys 157, 23, 1973

Mitchel, R., and Anderson, I.: Catalase Photoinactivation, Science 150, 74, 1965

Miyahara, T., Takeda, A., Hachimori, A., and Samejima, T.: On the Heterogeneity of Catalase from Goat Liver, J Biochem (Tokyo) 84, 1267, 1978

Murphy, J., and Maier, R.: Intracellular Distribution of Iron, Catalase, and Protein in Tomato Plant Tissue, J Agric Food Chem 15, 113, 1967

Nadler, V., Goldberg, I., and Hochman, A.: Comparative Study of Bacterial Catalases, Biochim Biophys Acta 882, 234, 1986

Nelson, D., and Niesow, L.: Enthalphy of Decomposition of Hydrogen Peroxide by Catalase at 25deg.C (With Molar Extinction Coefficients of $H_2O_2$ Solution in the UV, Anal Biochem 49, 474, 1972

Nicholls, P., and Schonbaum, G.: Catalases, The Enzymes, 2nd Ed. Vol. 7, P. Boyer, H. Lardy, and K. Myrback, Academic Press, NY, 147, 1963

Orr, C.: Studies on Ascorbic Acid. I. Factors Influencing the Ascorbate-Mediated Inhibition of Catalase, Biochem 6, 2995, 1967

Orr, C.: Studies on Ascorbic Acid. II. Physical Changes in Catalase Following Incubation with Ascorbate and Copper, Biochem 6, 3000, 1967

Oshino, N., Jamieson, D., Sugano, T., and Chance, B.: Optical Measurements of the Catalase-Hydrogen Peroxide Intermediate (Compound) in the Liver of Anaesthetized Rats and Its Implication to Hydrogen Peroxide Production, Biochem J 146, 67, 1975

Oshino, N., Oshino, R., and Chance, B.: The Characteristics of the "Peroxidatic" Reaction of Catalase in Ethanol Oxidation, Biochem J 131, 555, 1973

Percy, M., Dalton, A., Markovic, V., McLachlan, D., Hummel, J., Rusk, A., and Andrews, D.: Red Cell Superoxide Dismutase, Glutathione Peroxidase and Catalase in Down Syndrome Patients with and without Manifestations of Alzheimer Disease, Amer J Med Genetics 35, 459, 1990

Perrin, R., Briancon, S., Jeandel, C., Artur, Y., Minn, A., Penin, F., and Siest, G.: Blood Activity of Cu/Zn Superoxide Dismutase, Glutathione Peroxidase and Catalase in Alzheimer's Disease—A Case-Control Study, Gerontology 36, 306, 1990

Pitts, J. E.: Crystallization by Centrifugation, Nature 355, 117, 1992

Poznansky, M., and Chang, T.: Comparison of the Enzyme Kinetics and Immunological Properties of Catalase Immobilized by Microencapsulation and Catalase in Free Solution for Enzyme Replacement, Biochim Biophys Acta 334, 103, 1974

Pritchard, G., and Hudson, M.: Changes in Catalase Activity in Higher Plants and Fungi treated with Oxygen at High Pressure, Nature 214, 945, 1967

Rorth, M., and Jensen, P.: Determination of Catalase Activity by Means of the Clark Oxygen Electrode, Biochim Biophys Acta 139, 171, 1967

Rossman, M., and Labaw, L.: A Comparison of Electron Microscopy and X-Ray Diffraction Results for Ox Liver Catalase Crystals, J Mol Biol 29, 315, 1967

Sakamoto, T., and Higashi, T.: Studies on Rat Liver Catalase. VIII. Isolation and Translation of Catalase Messenger RNA, J Biochem (Tokyo) 76, 1227, 1974

Samejima, T., and Kita, M.: The Conformational Changes of Catalase Molecule Caused by Ligand Molecules, Biochim Biophys Acta 175, 24, 1969

Samejima, T., Kamata, M., and Shibata, K.: Dissociation of Bovine Liver Catalase at Low pH, J Biochem (Tokyo) 51, 181, 1962

Schroeder, W., Shelton, J., Shelton, J., Robberson, B., and Apell, G.: The Amino Acid Sequence of Bovine Liver Catalase: A Preliminary Report, Arch Biochem Biophys 131, 652, 1969

Scibior, D., and Czeczot, H.: Catalase: Structure, Properties, Functions, Postepy Hig Med Dosw (Online) Vol. 60, 170, 2006

Scott, M., Lubin, B., Zuo, L., and Kuypers, F.: Erythrocyte Defense Against Hydrogen Peroxide Preeminent Importance of Catalase, J Lab Clin Med 118, 7, 1991

Seah, T., and Kaplan, J.: Purification and Properties of the Catalase of Bakers' Yeast, J Biol Chem 248, 2889, 1973

Seah, T., Bhatti, A., and Kaplan, J.: Novel Catalytic Proteins of Bakers' Yeast. I. An Atypical Catalase, Can J Biochem 51, 1551, 1973

Sharma, K., Andersson, L., Loehr, T., Terner, J., and Goff, H.: Comparative Spectral Analysis of Mammalian, Fungal, and Bacterial Catalases. Resonance Raman Evidence for Iron-Tyrosinate Coordination, J Biol Chem 264, 12772, 1989

Shimizu, N., Kobayashi, K., and Hayashi, K.: The Reaction of Superoxide Radical with Catalase. Mechanism of the Inhibition of Catalase by Superoxide Radical, J Biol Chem 259, 4414, 1984

Spreti, N., Bartoletti, A., Di Profio, P., Germani, R., and Savelli, G.: Effects of Ionic and Zwitterionic Surfactants on the Stabilization of Bovine Catalase, Biotechnol Prog 11, 107, 1995

Sumner, J., and Dounce, A.: Crystalline Catalase, J Biol Chem 121, 417, 1937

Sumner, J., Dounce, A., and Frampton, V.: Catalase III, J Biol Chem 136, 343, 1940

Sund, H., Weber, K., and Molbert, E.: Dissociation of Beef Liver Catalase in its Subunits. German, Eur J Biochem 1, 400, 1967

Tanaka, K., Takeda, T., and Miyajima, K.: Cryoprotective Effect of Saccharides on Denaturation of Catalase by Freeze-Drying, Chem Pharm Bull (Tokyo) 39, 1091, 1991

Tanford, C., and Lovrien, R.: Dissociation of Catalase into Subunits, J Am Chem Soc 84, 1892, 1962

Tauber, H., and Petit, E.: Convenient Methods for Preparing Crystalline Catalase from Cow Liver, J Biol Chem 195, 703, 1952

Tudhope, G.: Red Cell Catalase in Health and in Disease with Reference to the Enzyme Activity in Anaemia, Clin Sci 33, 165, 1967

Vuilaume, M., Lafont, R., Hubert, M., Jouve, H., Calvayrac, R., and Best-Belpomme, M.: A New Property of Catalase: The Concerted Synthesis of Nucleotide Triphosphates, Bioelectrochem Bioenergetics 19, 541, 1988

Wheeler, C., Salzman, J., Elsayed, N., Omaye, S., and Korte, D.: Automated Assays for Superoxide Dismutase, Catalase, Glutathione Peroxidase, and Glutathione Reductase Activity, Anal Biochem 184, 193, 1990

Whiteside, C., and Hassan, H.: Role of Oxyradicals in the Inactivation of Catalase by Ozone, Free Radic Biol Med 5, 305, 1988

Yasukochi, Y., Nakamura, M., and Minakami, S.: Effect of Cobalt on the Synthesis and Degradation of Hepatic Catalase in vivo, Biochem J 144, 455, 1974

Zidoni, E., and Kremer, M.: Kinetics and Mechanism of Catalase Action. Formation of the Intermediate Complex, Arch Biochem Biophys 161, 658, 1974

The invention claimed is:

1. A method for the ozonolysis of unsaturated fatty acids and derivatives thereof, comprising:
    a) ozonolysis of the unsaturated fatty acid or derivative thereof in an organic phase comprising an organic solvent; and
    b) contacting the organic phase with an aqueous phase comprising catalase and optionally, a buffer;
    wherein the unsaturated fatty acid or the derivative thereof comprises at least one linear carbon chain of at least eight carbon atoms, and
    wherein at room temperature, the organic solvent separates as an organic phase when in the presence of an aqueous phase.

2. The method according to claim 1, further comprising contacting an aqueous phase with the organic phase during the ozonolysis.

3. The method according to claim 2, wherein the aqueous phase contacting the organic phase during ozonolysis is separated and removed from the organic phase prior to contacting the organic phase with the aqueous phase comprising catalase.

4. The method according to claim 1, wherein the unsaturated fatty acid or the derivative thereof is a compound of formula (I):

$$R^1-(CH_2)_x-CH=CH-(CH_2)_y-COR^2 \quad (I),$$

wherein
    $R^1$ is selected from the group consisting of hydrogen, HO—, HS—, CHO—, $R^2OC$—, unsubstituted or substituted alkyl, cycloalkyl, heterocycloalkyl, aryl and heteroaryl,
    $R^2$ is selected from the group consisting of HO—, substituted or unsubstituted alkoxy, alkenoxy, alkynoxy and cycloalkoxy having one to seven carbon atoms, —$NR^3R^4$, aryloxy and benzyloxy,
    $R^3$ and $R^4$ are each independently selected from the group consisting of hydrogen, alkyl, alkenyl, alkynyl, aryl and benzyl, and
    x and y, are each, independently, 0 or a larger integer.

5. The method according to claim 4, wherein
    $R^1$ is hydrogen,
    $R^2$ is HO—, methoxy or ethoxy, and
    a sum of x and y is nine or more.

6. The method according to claim 1, wherein the fatty acid or the derivative is at least one selected from the group consisting of oleic acid, erucic acid and esters thereof.

7. The method according to claim 1, wherein the organic solvent is at least one selected from the group consisting of compounds of formula:

$$R^5R^6R^7C-O-R^8$$

or intramolecular ethers thereof,
wherein
    $R^5$, $R^6$ and $R^7$ are each independently selected from the group consisting of hydrogen, an alkyl group of one to seven carbon atoms, a cycloalkyl group of one to seven carbon atoms, an unsubstituted aryl group and a substituted aryl group, and
    $R^8$ is selected from the group consisting of hydrogen, an alkyl, cycloalkyl, hydroxyalkyl or alkoxyalkyl group having one to seven carbon atoms, an unsubstituted aryl group, a substituted aryl group and a benzyl group.

8. The method according to claim 7, wherein the organic solvent is at least one a compound of formula $$R^5R^6R^7C-OH,$$

wherein $R^5$, $R^6$ and $R^7$ are independently selected from the group consisting of hydrogen, methyl, ethyl, propyl, butyl and pentyl.

9. The method according to claim 7, wherein at least one of $R^5$, $R^6$ and $R^7$ is methyl.

10. A method for the ozonolysis of unsaturated fatty acids and derivatives thereof, comprising:
    a) ozonolysis of the unsaturated fatty acid or derivative thereof in an organic phase comprising an organic solvent; and
    b) contacting the organic phase with an aqueous phase comprising catalase and optionally, a buffer;
    wherein the unsaturated fatty acid or the derivative thereof comprises at least one linear carbon chain of at least eight carbon atoms and,
    wherein the organic solvent is 2-methyl-2-butanol.

11. The method according to claim 1, wherein a volume per cent of the aqueous phase in contact with the organic phase, is from more than 0 to 50 percent of a total volume of the two phases.

12. The method according to claim 1, wherein the aqueous phase comprising catalase is in contact with the organic phase during the ozonolysis.

13. The method according to claim 1, wherein the catalase is beef liver catalase or a variant thereof.

14. The method according to claim 1, wherein the aqueous phase comprises a buffer and the pH of the aqueous phase before contacting with the organic phase, is from 3 to 11.

15. The method according to claim 14, wherein the pH of the aqueous phase before contacting with the organic phase, is from 5 to 8.

16. A method for removing reactive oxygen species from a reaction mixture comprising ozonolysis products of an unsaturated fatty acid or a derivative thereof and an organic solvent, comprising:
    contacting the reaction mixture with a catalase
    wherein said organic solvent, in the presence of an aqueous phase at room temperature, forms an organic phase separate from the aqueous phase.

17. The method according to claim 16, wherein the unsaturated fatty acid or the ester thereof is a compound of formula (I):

$$R^1-(CH_2)_x-CH=CH-(CH_2)_y-COR^2 \quad (I),$$

wherein
R¹ is selected from the group consisting of hydrogen, HO—, HS—, CHO—, R²OC—, unsubstituted or substituted alkyl, cycloalkyl, heterocycloalkyl, aryl and heteroaryl,
R² is selected from the group consisting of HO—, substituted or unsubstituted alkoxy, alkenoxy, alkynoxy and cycloalkoxy having one to seven carbon atoms, —NR³R⁴, aryloxy and benzyloxy,
R³ and R⁴ are each independently selected from the group consisting of hydrogen, alkyl, alkenyl, alkynyl, aryl and benzyl, and
x and y, are each, independently, 0 or a larger integer.

18. The method according to claim 16, wherein the organic solvent is selected from the group consisting of compounds having a formula:

or intramolecular ethers thereof,
wherein
$R^5$, $R^6$ and $R^7$ are each independently selected from the group consisting of hydrogen, an alkyl group of one to seven carbon atoms, a cycloalkyl group of one to seven carbon atoms, an unsubstituted aryl group and a substituted aryl group, and
$R^8$ is selected from the group consisting of hydrogen, an alkyl, cycloalkyl, hydroxyalkyl or alkoxyalkyl group having one to seven carbon atoms, an unsubstituted aryl group, a substituted aryl group and a benzyl group.

19. The method according to claim 18, wherein the organic solvent is 2-methyl-2-butanol.

* * * * *